(12) United States Patent
Farin et al.

(10) Patent No.: US 6,210,410 B1
(45) Date of Patent: Apr. 3, 2001

(54) COAGULATION DEVICE FOR COAGULATING BIOLOGICAL TISSUES

(75) Inventors: Günter Farin; Karl Ernst Grund, both of Tübingen (DE)

(73) Assignee: Erbe Elektromedizin GmbH (DE)

( * ) Notice: Subject to any disclaimer, the term of this patent is extended or adjusted under 35 U.S.C. 154(b) by 0 days.

(21) Appl. No.: 09/319,853

(22) PCT Filed: Dec. 11, 1997

(86) PCT No.: PCT/EP97/06937

§ 371 Date: Aug. 23, 1999

§ 102(e) Date: Aug. 23, 1999

(87) PCT Pub. No.: WO98/25530

PCT Pub. Date: Jun. 18, 1998

(30) Foreign Application Priority Data

Dec. 12, 1996 (DE) .............................. 196 51 7532
Dec. 19, 1996 (DE) .............................. 196 53 2140

(51) Int. Cl.[7] .................................................. A61B 18/18
(52) U.S. Cl. ........................ 606/49; 606/40; 219/121.51
(58) Field of Search ................... 606/40–42, 45–50; 219/121.5, 121.51

(56) References Cited

U.S. PATENT DOCUMENTS

| 4,060,088 | * | 11/1977 | Morrison, Jr. et al. | 606/40 |
| 5,122,138 | * | 6/1992 | Manwaring | 606/46 |
| 5,207,675 | * | 5/1993 | Canady | 606/40 |
| 5,720,745 | * | 2/1998 | Farin et al. | 606/49 |
| 6,039,736 | * | 3/2000 | Platt, Jr. | 606/49 |
| 6,063,084 | * | 5/2000 | Farin | 606/49 |

FOREIGN PATENT DOCUMENTS

| 41 39 029 | * | 6/1993 | (DE) . |
| 41 39 029 A1 | | 6/1993 | (DE) . |
| WO 97/11647 | * | 4/1997 | (WO) . |

* cited by examiner

*Primary Examiner*—Michael Peffley
(74) *Attorney, Agent, or Firm*—St. Onge Steward Johnston & Reens LLC

(57) ABSTRACT

Plasma coagulation devices are known in which a generally bare electrode wire is disposed in a tube that can be passed through the working channel of an endoscope until its end arrives in the field of view of the endoscope. Through the tube argon is supplied. A high-frequency current is supplied to produce a coagulation current in the form of an arc in the argon atmosphere between the end of the electrode wire and the portion of tissue to be coagulated. To simplify the arrangement and to improve its performance, in particular by reduction of the resistance to flow, it is proposed to supply the argon directly through the working channel and to use as conductor a wire insulated with thermally stable material, which at its end comprises a discharge section with a protective device to prevent a damaging direct flow of current into the portion of tissue to be coagulated.

15 Claims, 2 Drawing Sheets

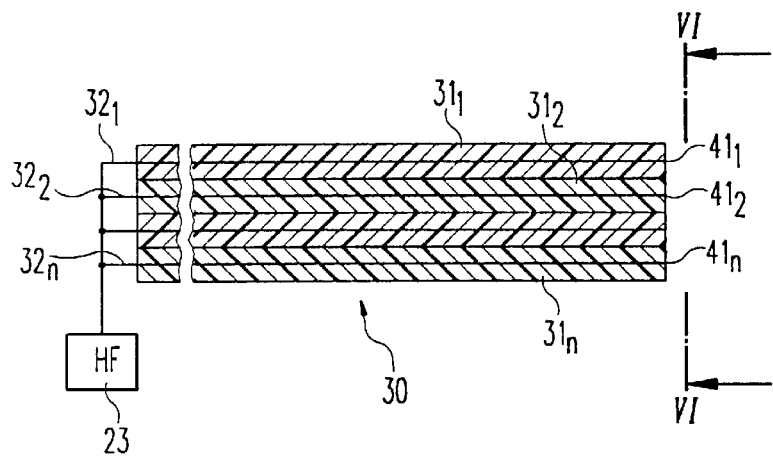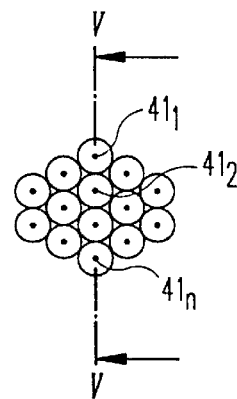
Fig. 5    Fig. 6
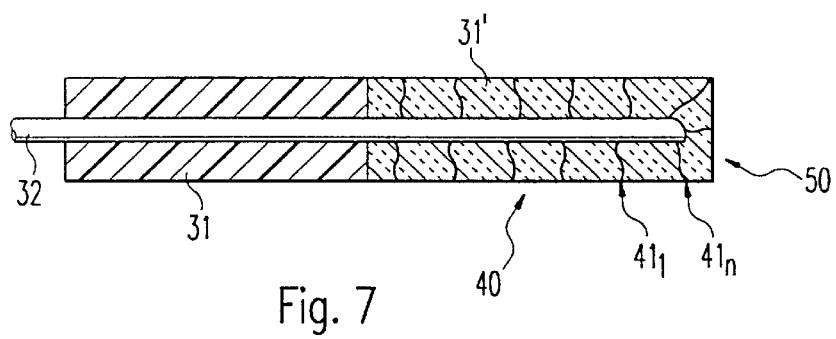
Fig. 7
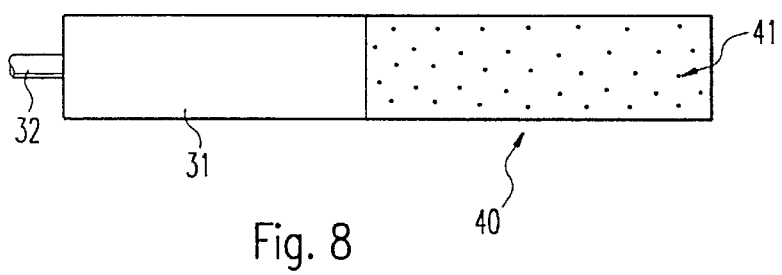
Fig. 8

COAGULATION DEVICE FOR COAGULATING BIOLOGICAL TISSUES

FIELD OF THE INVENTION

The invention relates to a coagulation apparatus, in particular a plasma coagulation apparatus.

BACKGROUND OF THE INVENTION

The German patent DE 37 10 489 C2 discloses a plasma coagulation apparatus intended for use in open surgery. In this apparatus argon is ejected from a nozzle in the center of which is a discharge electrode, with sufficient pressure and flow velocity that in addition to the coagulation effect produced by an arc formed between the electrode and the tissue to be coagulated, fluids "floating" on the tissue are pushed away. With this arrangement the risk of embolism is very high. Furthermore, it is extremely problematic to use this apparatus in body cavities because the large amounts of gas typically introduced in the cavities can lead to undesired insufflation effects.

A coagulation apparatus for use in an endoscope is known from U.S. Pat. No. 5,207,675. In this apparatus a tube, within which an electrode is slidably disposed, is inserted into the working channel of an endoscope in such a way that it can be manipulated within said channel by means of a handle, like an (ordinary) instrument. The electrode, which should simultaneously be constructed as an instrument, is kept in a state such that it projects from the tube when in the working (coagulating) mode, in which argon is expelled from the tube that houses the electrode. While in this state, if the electrode touches the tissue to be coagulated, considerable tissue damage can result. In the case of thin-walled tissues, the consequences (rupture, etc.) can be fatal.

In DE 195 35 811 A1 a coagulation apparatus of the kind cited above is described that goes some way toward avoiding the substantial problems associated with the arrangements just described. In particular, the end of the tube housing the electrode is so constructed that there is no danger of embolism even when a relatively strong gas stream is applied, during which time the electrode is withdrawn into the gas-emitting tube far enough that it cannot make direct contact with the tissue. However, this arrangement is relatively complicated to manufacture.

The object of the invention is to disclose a coagulation apparatus that ensures increased safety in use and improved operation, while reducing the manufacturing complexity and cost.

SUMMARY OF THE INVENTION

An essential point of the invention is that it departs completely from the idea that (noble) gas must be aimed directly at the site where coagulation is occurring, i.e. by means of a tube within which the current-supplying electrode is disposed. Instead, in the present invention the working channel itself is used as a conduit to transport the gas, while the electrode can be constructed as a fully insulated wire with no lumen. Surprisingly, it has been found that no disadvantageous effects are introduced by the fact that the gas emerges from an end of the working channel proximal to the distal end of the conductor—that is, proximal to the discharge section—and that the discharge section occupies no precisely specified position with respect to the end of the working channel, from which the gas emerges. On the other hand, it is considerably simpler to construct the conductor as an insulated wire without a lumen, which reduces the costs of manufacture and enables disposable conductors to the used. This in turn reduces the risk of infection.

Furthermore, conductors without a lumen are not only simpler to manufacture but, because conductors have small diameters it's possible for the coagulation apparatus incorporating such conductors to be further miniaturized as a whole. At the same time, however, a considerably larger cross section for flow through the gas-supply conduit is ensured, which offers the advantage that the regulation of the gas supply can be substantially improved in the simplest possible manner. That is, the gas pressure at the distal end of the working channel can be assumed to differ only negligibly from the gas pressure at its proximal end, because with the large flow cross sections achievable here, only a slight pressure drop (given the customary, not too large flow velocities) is to be expected. Hence it is possible simultaneously (with appropriate regulation of the gas-supply pressure) to eliminate in advance the danger that, if the gas does not flow away as intended, an uncontrolled, damaging insufflation will occur.

With absolute certainty the possibility is avoided that an excessively strong laminar gas stream will strike the region of the tissue to be coagulated, which, as mentioned, could cause an embolism.

Preferably the conductor comprises at least one wire, which by means of a closely apposed layer of insulation is insulated in particular from the endoscope, i.e. the wall of the working channel. The arrangement described here is thus particularly simple to manufacture. Preferably in this case the wire is chosen to be stiffly elastic so that proximal fixation of the conductor also ensures adequate fixation of its distal end and hence of the discharge section. It is therefore not necessary to guide the conductor so that it is precisely coaxial with the working channel and, in particular, to keep it exactly in position in the end region, because—surprisingly—the preferably gently outflowing current of noble gas forms a kind of "cloud" that fills the region between the discharge section and the tissue to be coagulated.

The layer of insulation is preferably so constructed that a specific capacitance, preferably matched to the frequency of the coagulation current, is produced between conductor and wall, so that optimal performance can be ensured. In particular, the capacitance (stray capacitance) between conductor and wall should be kept very low in order to minimize losses.

Preferably the insulation layer consists of thermally stable material, in particular polytetrafluoroethylene or a similar plastic resistant to high temperatures.

The protective device is preferably so constructed that a substantially undirected discharge at the discharge section is ensured. This measure is intended to make certain that the discharge current flows between the discharge section and a section of the tissue with a relatively high moisture content and hence a relatively low resistance (per unit area). As a result, it is ensured that the coagulation current "finds its way" automatically from the discharge section. An especially uniform and rapid coagulation effect can thus be guaranteed.

There are various possible ways to construct the protective device in such a way that no excessively large, potentially damaging coagulation currents will flow.

In a first embodiment of the invention the protective device is formed directly by the insulation layer, inasmuch as the ends thereof project beyond the current-conducting part (in the direction of the conductor). Many geometrical shapes are conceivable here.

the protective device can be constructed as a separate part, in particular as a sheath-, ball- or basket-shaped part made of insulating, thermally stable material. Ceramic material is especially suitable for this purpose.

Preferably the discharge section comprises substantially punctate or tip-shaped discharge electrodes. This measure ensures easy ignition of the plasma owing to the high field strengths at the pointed tips. It also increases safety in operation, because it is not necessary to use too-high voltages to trigger the discharge.

In an especially preferred embodiment of the invention the discharge section comprises a plurality of discharge electrodes arranged in parallel electrically and substantially defining a continuous surface, in which the electrodes are substantially equidistant from one another and separated by layers of insulation. When such uniformly distributed, punctate electrodes are used, which in addition are disposed substantially in a plane or in a convex surface, preferably flush with the end surface of the insulation, it is ensured that even if the electrodes make direct contact with the tissue, no serious damage to the tissue will result. The reason is that with an arrangement of this kind a substantially hemispherical current distribution is formed in the region of the contact area of each punctate electrode (the contact is limited to the surface of the tissue and the electrode cannot penetrate into the tissue), which in turn causes the current density to become so low, even a very short distance away from the electrode, that no serious tissue damage can occur. In the direct contact region, where the current density is still relatively high and the liquid contained in the tissue vaporizes, the resistance rises very rapidly, so that the current flow is completely cut off. Because a plurality of individual electrodes is provided it can be ensured that a uniform plasma coagulation current flows over a relatively large area.

Preferably fixation and/or adjustment devices are provided, in particular at the proximal end of the endoscope, and are so constructed that the discharge section is positioned in the field of view of the observation optics of the endoscope.

In another preferred embodiment of the invention the fixation and adjustment devices are constructed in the manner customary for instruments that can be introduced into the working channel of endoscopes and can be moved or manipulated while projecting out of the distal end of said channel. The actual manipulation mechanism is situated at the end of the endoscope away from the patient and is so constructed that the distal end of the conductor with the discharge section can be moved within the field of view of the endoscope. In this way a precise treatment of the tissue can be carried out, while the endoscope is immobile relative to the tissue.

BRIEF DESCRIPTION OF THE DRAWINGS

In the following, preferred embodiments of the invention are described with reference to drawings, wherein FIG. 5 shows a fourth embodiment of a discharge section, with a plurality of electrodes in longitudinal section, FIG. 6 is a view of the discharge section according to FIG. 5 along the line VI—VI, FIG. 7 is a view of a fifth embodiment of a discharge section, with a plurality of electrodes in longitudinal section, and FIG. 8 is a side view of the discharge section according to FIG. 7.

DETAILED DESCRIPTION

Figure 1:
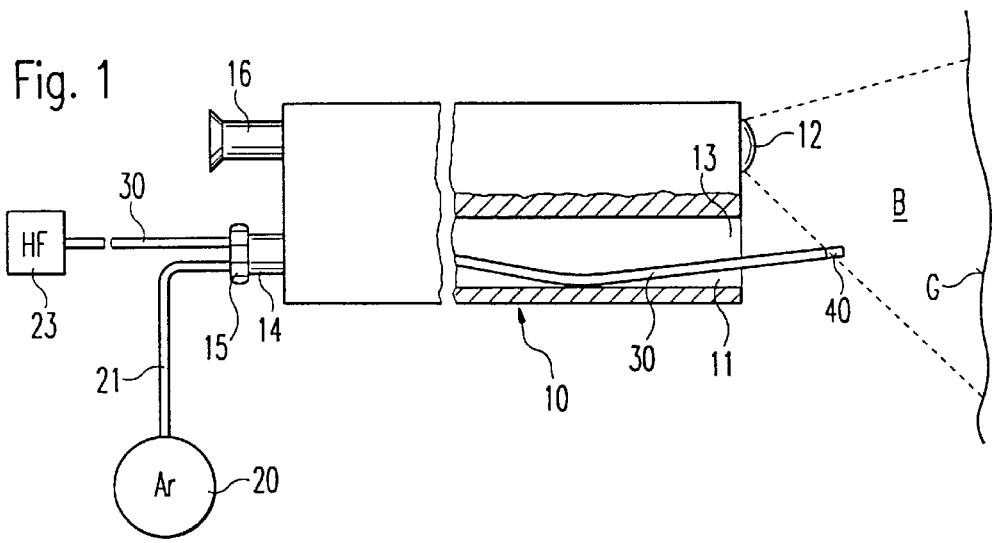
FIG. 1 is a schematic partially sectional view of an endoscope with partially opened working channel.

In the following description, the same reference numerals are used for identical parts or parts with identical actions.

In FIG. 1 a highly schematic side view of an endoscope 10 is shown, which in a manner known per se comprises a working channel 11, which extends from a proximal working-channel end 14 to a distal working-channel end 13. At the distal end of the endoscope 10 an optic 12 is provided, through which objects in the region of a field of view B, in particular tissue G to be coagulated, are imaged, in general on a television screen. In the present case, for purposes of illustration an ocular 16 at the proximal end of the endoscope 10 is shown.

At the proximal end 14 of the working channel 11 a Y-piece 15 is disposed, by way of which, firstly, a conduit 21 is connected in a gas-tight manner. The conduit 21 leads to an argon source 20 that comprises regulatory devices (not shown) in order to allow a pre-adjustable, uniform current of argon gas to flow into the proximal end 14 of the working channel 11, so that at the distal working-channel end 13 the argon flows out uniformly with low velocity, as a "turbulent cloud", and fills the region between a tissue G to be coagulated and a distal discharge section 40, which forms the end of a conductor 30. The conductor 30 in turn runs through the working channel 11 and extends (by way of a sealing element) through the Y-piece 15 to an HF source 23. The HF source 23 is constructed in a manner known per se and enables a high-frequency coagulation current to be sent through the conductor 30 to the discharge section 40. HF generators of this kind are commercially obtainable.

In the following, particular embodiments of the discharge section will be described in more detail with reference to FIGS. 2 to 6.

Figure 2:
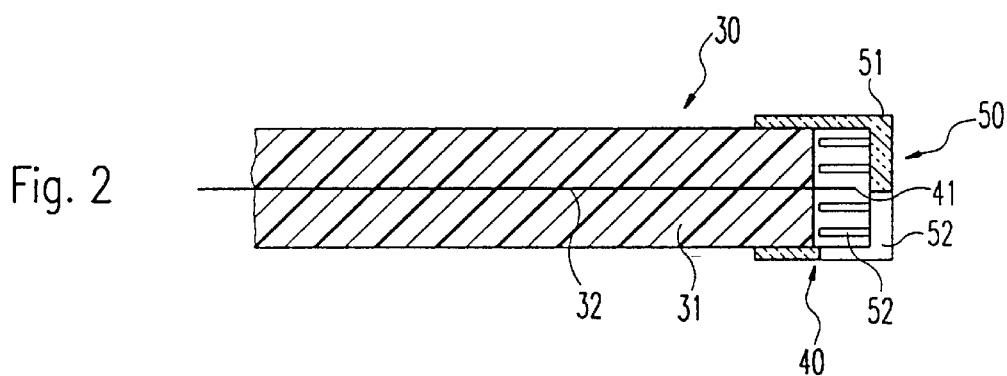
FIG. 2 shows a first embodiment of a discharge section with protective device in longitudinal section.
Figure 3:
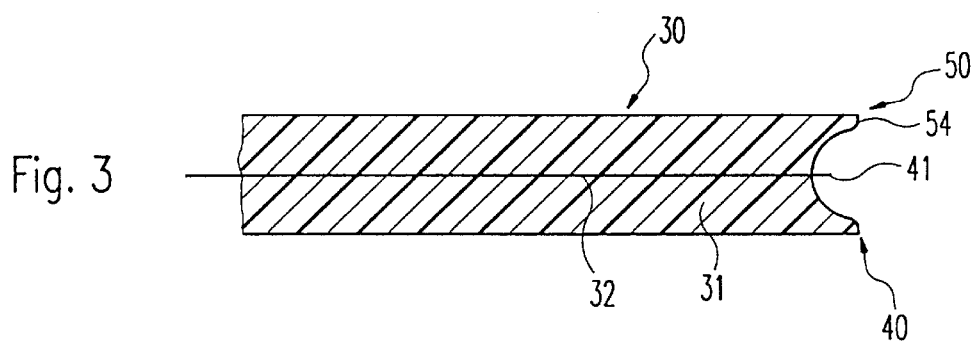
FIG. 3 shows a second embodiment of a discharge section with protective device in longitudinal section.
Figure 4:
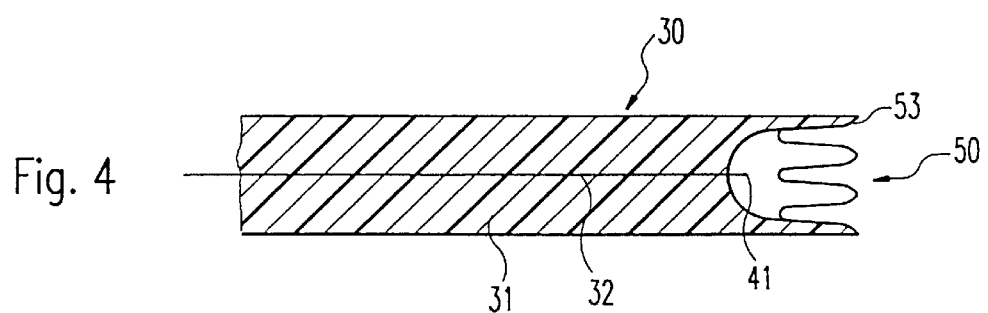
FIG. 4 shows a third embodiment of a discharge section with protective device in longitudinal section.

From FIGS. 2 to 4 it can be seen that the conductor 30 comprises a wire 32 enclosed in an insulation layer 31, preferably made of PTFE. The wire 32 with the surrounding insulation layer 31 is sufficiently stiff that, as shown in FIG. 1, it is held by the immobilizing Y-piece 15 at the proximal end in a position such that its discharge section 40 is kept in a specific position within the field of view B of the optic 12, so that the latter position remains substantially constant even during movement of the endoscope 10.

In the embodiment of the invention shown in FIG. 2 the wire 32 is so disposed as to project beyond the end of the insulation layer 31, so that a discharge electrode 41 is formed. Preferably this electrode is pinched off or sharpened in such a way as to produce sharp edges, at which the electrical field strength (as is known per se) is very high, so that ignition of the plasma is possible even with relatively low voltages.

Now, in order to prevent the discharge electrode 41 from coming into direct, current-conducting contact with the tissue G to be coagulated, which could produce serious and dangerous tissue damage (or even rupture, in the case of thin tissue layers), a protective device 50 in the form of a basket 51 is provided, which in this case is made of non-conducting ceramic material that is resistant to high temperatures. The basket 51 comprises openings 52 so that direct gas contact is possible between the external surroundings and the interior of the basket, and a substantially undisturbed current flow through a plasma can develop.

In the embodiments of the invention shown in FIGS. 3 and 4 the protective device 50 is formed by the material of which the insulation layer 31 is composed. In the embodiment of the invention shown in FIG. 3, the discharge section 50 is partially cut away for this purpose so that its end is concave and the discharge electrode 41 is situated at the base of the concavity; the edge 54 of the concavity projects in the distal direction beyond the discharge electrode 41. This arrangement ensures that no direct contact can occur between the discharge electrode 41 and a tissue G to be coagulated.

In the embodiment shown in FIG. 4 the principle is similar but the edge 54 is not smooth; instead it comprises a row of teeth 53, which likewise prevent direct contact between the discharge electrode 41 and the tissue G to be coagulated.

The preferred embodiment of the invention shown in FIGS. 5 and 6 is based on a different principle for the protective device 50. In this arrangement a whole bundle of conductors $32_1, 32_2, \ldots, 32_n$ with surrounding insulation layers $31_1, 31_2, \ldots, 31_n$ is provided, in which the conductors 32 are connected in parallel to the HF source 23. The conductors 30 are cut off at the distal end so as to define a planar surface (in another embodiment, a convex surface), so that the ends of the wires 32 form punctate discharge electrodes $41_1, 41_2, \ldots, 41_n$ that are flush with the end surfaces of the insulation layers 31. If such an end surface, formed by an area of insulation within which punctate discharge electrodes 41 are equidistantly distributed (as shown in FIG. 6), comes into contact with a tissue G, the resulting current flow extends hemispherically from each of the punctate contact sites, such that the current density decreases as the reciprocal of the third power of the distance from the punctate electrode. As a result it is ensured that even at very small depths within the tissue an "innocuous" current density prevails.

the embodiment of the invention shown in FIG. 7 a plurality of punctate discharge electrodes $41_1, 41_n$ is again provided, which are flush with the end surface of an insulation layer 31'. The insulation layer 31' in this case is constructed as a ceramic part in which the discharge electrodes are embedded in the form of filling. This arrangement ensures that—as shown in FIG. 8—an area relatively densely packed with discharge electrodes 41 is produced, so that the plasma discharge can be generated at the discharge section 40 in an undirected manner. In another embodiment of the invention, not shown here, the discharge section 40 is made of a (metallic) conductor piece coated with a thin insulating layer in which small openings or holes are made, to form the punctate discharge electrodes.

It will be evident from the above that an essential point of the present invention lies in the fact that it no longer employs—as was previously customary—a "tube" with electrode or current-supply device contained therein, through which the noble gas is "blown" directly into the region in which the discharge is to occur; instead, the working channel itself is used and the noble gas is, so to speak, unspecifically (with respect to the discharge region) supplied. In turn, the site from which the discharge "begins" is precisely specified and can very easily be adjusted, so that the operating physician has control of the coagulation process substantially without difficult manipulations.

What is claimed is:

1. Coagulation apparatus comprising
   an endoscope working channel with a proximal opening and a distal opening and an inner surface extending between the proximal and distal openings;
   a current-supply device with a conductor to conduct a coagulation current from a source to a discharge section at a distal end of the conductor;
   a gas-supply conduit to guide gas from a gas source to a space between the discharge section and a portion of tissue to be coagulated;
   a protective device at the discharge section to prevent a damaging direct flow of current between the discharge section and the portion of tissue to be coagulated;
   wherein the gas-supply conduit is formed by the endoscope working channel, and the conductor passing through the endoscope working channel and having an outer insulating layer, which is spaced radially inwardly from the inner surface of the endoscope working channel at least in the vicinity of the distal opening, the distal end of the conductor projecting out of the distal opening with its distal end and its discharge section, in such a way that gas emerging through the distal opening flows around the distal end of the conductor and the discharge section as it passes into the space between the discharge section and the portion of tissue to be coagulated.

2. Coagulation apparatus according to claim 1, characterized in that the conductor (30) comprises at least one wire (32) that is insulated, in particular with respect to the endoscope (10) or the wall of the working channel (11), by means of the closely apposed insulation layer (31).

3. Coagulation apparatus according to claim 2, characterized in that the at least one wire is stiffly elastic in such a way that a proximal fixation of the conductor ensures adequate fixation of the discharge section.

4. Coagulation apparatus according to claim 2, characterized in that the insulation layer (31) is made sufficiently thick that a specified capacitance, preferably matched to the frequency of the coagulation current, is produced between conductor and wall.

5. Coagulation apparatus according to claim 2, characterized in that the insulation layer is made of thermally stable material, in particular of polytetrafluoroethylene.

6. Coagulation apparatus according to claim 1, characterized in that the protective device is so constructed as to ensure a substantially undirected discharge at the discharge section.

7. Coagulation apparatus according to claim 1, characterized by a manipulation mechanism so constructed and so disposed in functional connection with the conductor that the distal end of the conductor can be moved in the manner of an endoscope operating instrument.

8. Coagulation apparatus comprising:
   an endoscope working channel with a proximal opening and a distal opening;
   a current-supply device with a conductor to conduct a coagulation current;
   a gas-supply conduit to guide gas from a gas source through the endoscope working channel towards a portion of tissue to be coagulated;
   the conductor having an insulation layer and at least one wire embedded in the insulation layer, which has a distal end extending beyond a distal discharge section of the one wire to prevent a damaging direct flow of current between the distal discharge section and the portion of tissue to be coagulated, the gas emerging through the distal opening flows around the distal end of the insulation layer as it passes into the space between the distal end and the portion of tissue to be coagulated.

9. Coagulation apparatus according to one of the preceding claims, characterized in that the protective device (50) is formed as a separate part made of insulating, thermally stable material, in particular of ceramic.

10. Coagulation apparatus comprising an endoscope working channel with a proximal and a distal opening;

a current-supply device with a conductor to conduct a coagulation current from a source to a discharge section at a distal end of the conductor;

a gas-supply conduit to guide gas from a gas source to a space between the discharge section and a portion of tissue to be coagulated; the conductor having substantially sharp-tipped discharge electrodes and a protective device at the discharge section to prevent a damaging direct flow of current between the discharge section and the portion of tissue to be coagulated;

wherein the gas-supply conduit is formed by the endoscope working channel, and the conductor passing through the endoscope working channel projects out of the distal opening thereof with its end and its discharge section, in such a way that gas emerging through the opening flows around the distal end of the conductor and the discharge section as it passes into the space between the discharge section and the portion of tissue to be coagulated.

11. Coagulation apparatus according to claim 10, characterized in that a plurality of discharge electrodes is provided, disposed so as to be electrically in parallel and substantially to define a continuous surface.

12. Coagulation apparatus according to claim 11, characterized in that the discharge electrodes are disposed in a plane.

13. Coagulation apparatus according to claim 11, characterized in that the discharge electrodes are disposed in a convex surface.

14. Coagulation apparatus according to claim 10, characterized in that the discharge electrodes are disposed substantially flush with an insulation layer.

15. Coagulation apparatus according to claim 10, characterized in that the discharge electrodes comprise a plurality of insulated individual wires, each of which forms a planar surface at its end.

* * * * *